(12) United States Patent
Huang et al.

(10) Patent No.: US 9,366,624 B2
(45) Date of Patent: Jun. 14, 2016

(54) APPARATUS FOR MEASURING TURBIDITY AND METHOD FOR RAPIDLY MEASURING TURBIDITY

(71) Applicant: SINSCHE TECHNOLOGY (HONGKONG) CO., LIMITED, Hong Kong (HK)

(72) Inventors: Xiaoping Huang, Hong Kong (HK); Dan Gao, Hong Kong (HK); Jianming Ruan, Hong Kong (HK); Chuhui Huang, Hong Kong (HK); Liping Hu, Hong Kong (HK)

(73) Assignee: SHENZHEN SINSCHE TECHNOLOGY CO., LTD., Shenzhen (CN)

( * ) Notice: Subject to any disclaimer, the term of this patent is extended or adjusted under 35 U.S.C. 154(b) by 0 days.

(21) Appl. No.: 14/616,757

(22) Filed: Feb. 9, 2015

(65) Prior Publication Data

US 2015/0241343 A1    Aug. 27, 2015

(30) Foreign Application Priority Data

Feb. 25, 2014    (CN) .......................... 2014 1 0064219

(51) Int. Cl.
| G01N 21/00 | (2006.01) |
| G01N 21/51 | (2006.01) |
| G01N 21/47 | (2006.01) |

(52) U.S. Cl.
CPC ............ *G01N 21/51* (2013.01); *G01N 21/4785* (2013.01); *G01N 2021/513* (2013.01); *G01N 2201/061* (2013.01)

(58) Field of Classification Search
CPC combination set(s) only.
See application file for complete search history.

(56) References Cited

U.S. PATENT DOCUMENTS 4,997,769 A * 3/1991 Lundsgaard ........... G01N 21/31
356/328

\* cited by examiner

*Primary Examiner* — Tri T Ton

(57) ABSTRACT

Disclosed is an apparatus for measuring turbidity, which includes a body case and includes a light source device, a light path absorption cell, a light path reception and detection module, a screen and a central processing unit, all of which are disposed on the body case. Spectrum of the light ray emitted by the light source device mainly has wavelengths in a range of 350 nm to 1000 nm. The spectrum has two peak wavelengths, one of which is in a range of 400 nm to 500 nm and has a half-peak width in a range of 5 nm to 50 nm, and the other of which is in a range of 550 nm to 750 nm and has a half-peak width in a range of 50 nm to 150 nm. Also disclosed is a method for rapidly measuring turbidity. By means of the present invention, turbidity of water sample can be measured accurately, simply, steadily and in high sensitivity.

2 Claims, 2 Drawing Sheets

| Standard Points | Preparing Method |
|---|---|
| 10NTU | 2.5ml of turbidity standard solution + pure water + 44g of P15 + pure water and capacity to the mark of 1000ml |
| 20NTU | 5ml of turbidity standard solution + pure water + 44g of P15 + pure water and capacity to the mark of 1000ml |
| 40NTU | 10ml of turbidity standard solution + pure water + 44g of P15 + pure water and capacity to the mark of 1000ml |
| 200NTU | 25ml of turbidity standard solution+ pure water + 50g of P15 + pure water and capacity to the mark of 500ml |
| 500NTU | 25ml of turbidity standard solution + pure water + 20g of P15 + pure water and capacity to the mark of 200ml |
| 800NTU | 50ml of turbidity standard solution + pure water + 25g of P15 + pure water and capacity to the mark of 250ml |

FIG. 3

APPARATUS FOR MEASURING TURBIDITY AND METHOD FOR RAPIDLY MEASURING TURBIDITY

CROSS-REFERENCE TO RELATED APPLICATIONS

This present invention claims the benefit of Chinese Patent Application No. CN201410064219.8, filed on Feb. 25, 2014; the contents of which are hereby incorporated by reference.

FIELD OF THE INVENTION

The present invention relates to the technology field of environmental monitoring, in particular, it concerns an apparatus for measuring turbidity and a method for rapidly measuring turbidity.

BACKGROUND OF THE INVENTION

Turbidity is an index to token the concentration of suspended particles and colloid in water, which can reflect the suspended particles content in water. The contents of bacteria, coliform, virus, ferro-manganese and so on in water can be reduced by reducing the turbidity of water, thus the turbidity of water is an important water quality index for water treatment. Thus, according to GB 5749-2006 Standards for Drinking Water Quality, turbidity is classed as a conventional index of water quality and its limiting value is 1 NTU.

Measuring technique of turbidity has a long history of development—from candle method to photometer and then to turbidimeter. At present, there are two measuring methods of international standard as follows: one is the "USEPA 180.1" and the other one is the "ISO7027". The former is achieved by using a tungsten lamp as light source with a spectrum in a range of 400 nm to 600 nm, and it has poor stability and narrow range of testing; and the latter is achieved by using a LED as light source with a wavelength of 860 nm, and it has good testing stability but has low sensitivity for the water sample with low turbidity and especially for the one with turbidity less than 1 NTU.

SUMMARY OF THE INVENTION

One object of the present invention is to provide an apparatus for measuring turbidity and a method for rapidly measuring turbidity, so as to measure turbidity of water sample accurately, simply, steadily and in high sensitivity.

To achieve the above object, the present invention provided an apparatus for measuring turbidity, which includes a body case and further comprising a light source device, a light path absorption cell, a light path reception and detection module, a screen and a central processing unit, all of which are disposed on the body case. The light path reception and detection module and the screen are connected with the central processing unit and light ray emitted by the light source device is absorbed by the light path reception and detection module after passing the light path absorption cell. Spectrum of the light ray emitted by the light source device has wavelengths mainly in a range of 350 nm to 1000 nm; the spectrum has two peak wavelengths, one of which is in a range of 400 nm to 500 nm and has a half-peak width in a range of 5 nm to 50 nm, and the other of which is in a range of 550 nm to 750 nm and has a half-peak width in a range of 50 nm to 150 nm.

Preferably, the light path absorption cell includes a hollow cylinder which is perpendicular to surface of the body case and extends upwardly; and a sealed cap is provided at the top of the hollow cylinder.

To achieve the above object, the present invention provided a further method for rapidly measuring turbidity, which includes the steps of:

(1) Preparing turbidity standard solution: dissolving 2.50 g of hydrazine sulfate in pure water and capacity to the mark of 250 ml; dissolving 25.0 g of hexamethylenetetramine in pure water and capacity to the mark of 250 ml, mixing both of which and then keeping it away from the light for 24 hours at a temperature of 2° C. to 28° C.;

(2) Drawing calibration curve: diluting the prepared turbidity standard solution into several standard solutions according to different standard points, adding these standard solutions into an apparatus for measuring turbidity one by one, and then drawing a calibration curve and storing the calibration curve;

(3) Measuring turbidity of water sample: adding water sample into the apparatus to measure the turbidity, working out turbidity of the water sample by means of the calibration curve and then displaying relevant result on the screen directly.

Compared with the prior art, the present invention has at least following beneficial effects: according to the present invention, the apparatus for measuring turbidity includes a light source, the spectrum of which has a wavelength mainly in a range of 350 nm to 1000 nm and has two peak wavelengths, one of which is in a range of 400 nm to 500 nm and has a half-peak width in a range of 5 nm to 50 nm, and the other of which is in a range of 550 nm to 750 nm and has a half-peak width in a range of 50 nm to 150 nm. By means of such a light source, not only the water sample with turbidity less than 1 NTU but also the water sample with turbidity of 1000 NTU can be measured. The apparatus of the present invention has good stability, high sensitivity and wider range of testing. And the method of the present invention is simple.

BRIEF DESCRIPTION OF THE DRAWINGS

FIG. 3 is a reference table shows how to dilute turbidity standard solution into several standard solutions according to different standard points, according to an embodiment of the method for rapidly measuring turbidity of the present invention.

DETAILED DESCRIPTION OF ILLUSTRATED EMBODIMENTS

It should be noted that the embodiments and features of the embodiments can be combined with each other on condition that they do not conflict with each other. The technical solutions of embodiments will be clearly and completely described as follows by combining the accompanying drawing.

Figure 1:
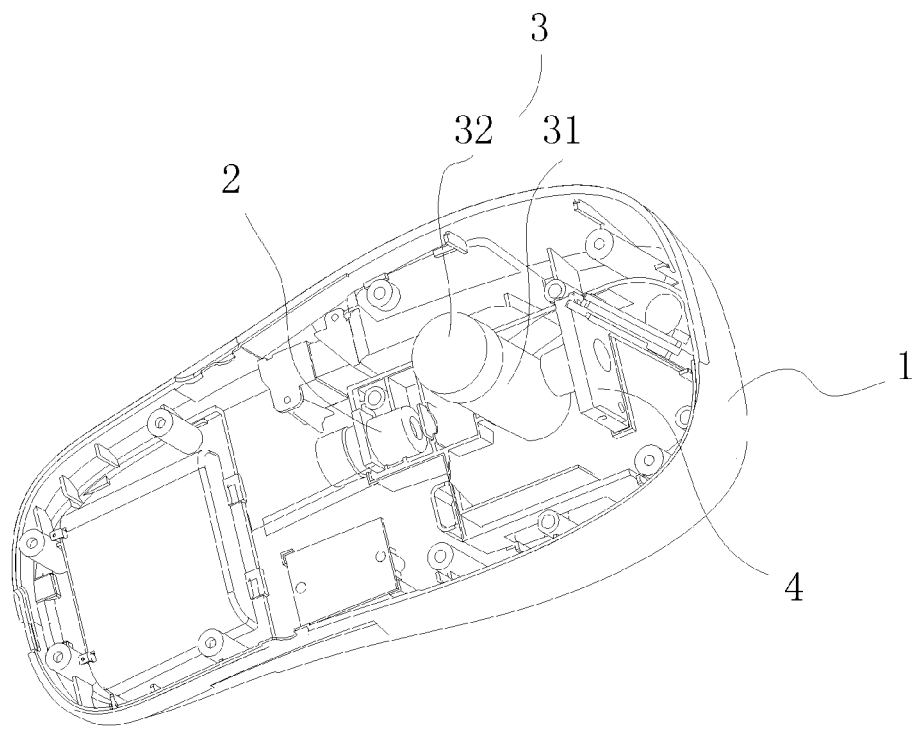
FIG. 1 is a first structure diagram of an apparatus for measuring turbidity according to an embodiment of the present invention.
Figure 2:
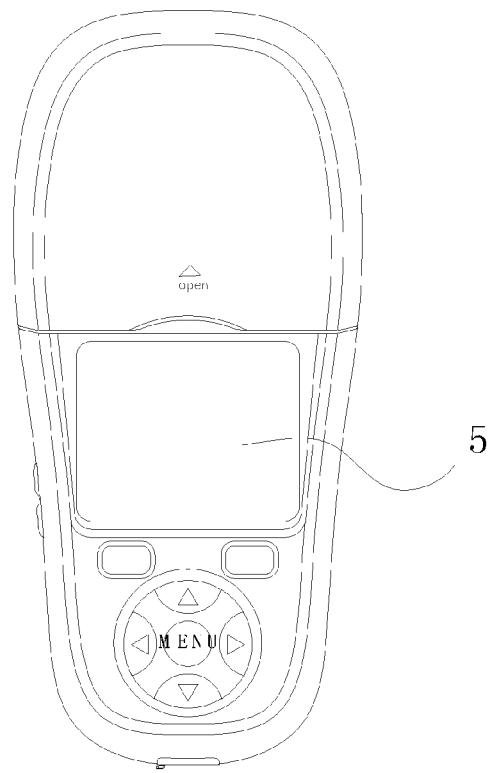
FIG. 2 is a second structure diagram of an apparatus for measuring turbidity according to an embodiment of the present invention.

As shown in FIG. 1 and FIG. 2, according to an embodiment of the present invention, the apparatus for measuring turbidity includes a body case 1 and further includes a light source device 2, a light path absorption cell 3, a light path reception and detection module 4, a screen 5 and a central processing unit, all of which are disposed on the body case 1. Both of the light path reception and detection module 4 and the screen 5 are connected with the central processing unit. The light path absorption cell 3 includes a hollow cylinder 31 which is perpendicular to surface of the body case 1 and extends upwardly; and a sealed cap 32 is provided at the top of the hollow cylinder 31. The top opening of the hollow cylinder 310 can be sealed by the sealed cap 32 after water sample is loaded into the light path absorption cell 3, thus it can prevent the water sample from spilling which will lead to pollution. When light ray emitted by the light source device 2 are absorbed and detected by the light path reception and detection module 4 after passing the light path absorption cell 3, turbidity of the water sample will be figured out by the light path reception and detection module 4 by means of a preset calibration curve; and the relevant result will be displayed on the screen 5 directly.

When the light ray emitted by the light source device 2 passing the light path absorption cell 3, intensity of the light ray suffers from attenuation due to absorption and scattering process. At the same time, measure the intensities of transmission light and scattered light of the light beam which is projected onto the water sample and then determine the turbidity of the water sample according to a ratio between the intensities of transmission light and scattered light. Both of stability and sensitivity of the turbidity measurement depend on a spectrum of the light emitted by the light source device 2.

Spectrum of the light ray emitted by the light source device 2 has wavelengths mainly in a range of 350 nm to 1000 nm; the spectrum has two peak wavelengths, one of which is in a range of 400 nm to 500 nm and has a half-peak width in a range of 5 nm to 50 nm, and the other of which is in a range of 550 nm to 750 nm and has a half-peak width in a range of 50 nm to 150 nm. Thus it can overcome the disadvantages of two measuring methods of international standard. By means of such a light source, not only the water sample with turbidity less than 1 NTU but also the water sample with turbidity of 1000 NTU can be measured. The apparatus of the present invention has good stability, high sensitivity and wider range of testing. And the method of the present invention is simple.

According to an embodiment of the present invention, the method for rapidly measuring turbidity includes following steps:

(1) Preparing turbidity stander solution with turbidity of 4000 NTU: dissolving 2.50 g of hydrazine sulfate in pure water and capacity to the mark of 250 ml; dissolving 25.0 g of hexamethylenetetramine in pure water and capacity to the mark of 250 ml; mixing both of which and then keeping it away from the light for 24 hours at a temperature of 2° C. to 28° C.;

(2) Drawing calibration curve: as shown in FIG. 3, diluting the prepared turbidity standard solution into several standard solutions according to different standard points, adding these standard solutions into the apparatus of the present invention for measuring turbidity one by one, and then drawing a calibration curve and storing the calibration curve; and (3) Measuring turbidity of water sample: adding water sample into the apparatus for measuring turbidity, working out turbidity of the water sample by means of the calibration curve and then displaying relevant result on the screen directly.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and scope of the invention.

What is claimed is:

1. An apparatus for measuring turbidity comprising a body case (1) and further comprising a light source device (2), a light path absorption cell (3), a light path reception and detection module (4), a screen (5) and a central processing unit, all of which are disposed on the body case (1), Both of light path reception and detection module (4) and the screen (5) being connected with the central processing unit and light ray emitted by the light source device being absorbed by the light path reception and detection module (4) after passing the light path absorption cell (3), wherein, spectrum of the light ray emitted by the light source device (2) has wavelengths in a range of 350 nm to 1000 nm; the spectrum has two peak wavelengths, one of the two peak wavelengths is in a range of 400 nm to 500 nm and has a half-peak width in a range of 5 nm to 50 nm, and the other of the two peak wavelengths is in a range of 550 nm to 750 nm and has a half-peak width in a range of 50 nm to 150 nm.

2. The apparatus for measuring turbidity according to claim 1, wherein the light path absorption cell (3) comprises a hollow cylinder (31) which is perpendicular to surface of the body case (1) and extends upwardly; and a sealed cap (32) is provided at the top of the hollow cylinder (31).

\* \* \* \* \*